United States Patent
Niijima (10) Patent No.: US 8,492,543 B2
(45) Date of Patent: Jul. 23, 2013

(54) METHOD FOR PRODUCING QUINAZOLINE DERIVATIVE

(75) Inventor: Jun Niijima, Tsukuba (JP)

(73) Assignee: Eisai R&D Management Co., Ltd., Tokyo (JP)

(*) Notice: Subject to any disclaimer, the term of this patent is extended or adjusted under 35 U.S.C. 154(b) by 423 days.

(21) Appl. No.: 12/733,169

(22) PCT Filed: Aug. 15, 2008

(86) PCT No.: PCT/JP2008/064620
§ 371 (c)(1), (2), (4) Date: May 10, 2010

(87) PCT Pub. No.: WO2009/025238
PCT Pub. Date: Feb. 26, 2009

(65) Prior Publication Data
US 2011/0152521 A1  Jun. 23, 2011

(30) Foreign Application Priority Data
Aug. 17, 2007 (JP) ................ P2007-212921

(51) Int. Cl.
*C07D 239/72* (2006.01)
(52) U.S. Cl.
USPC ..................... 544/283; 544/284
(58) Field of Classification Search
USPC ............................. 544/283, 284
See application file for complete search history.

(56) References Cited

U.S. PATENT DOCUMENTS

| | | | |
|---|---|---|---|
| 5,385,907 A | 1/1995 | Asakura et al. | |
| 6,352,989 B1 | 3/2002 | Miyazaki et al. | |
| 6,740,662 B1 | 5/2004 | Iwata et al. | |
| 6,800,644 B2 | 10/2004 | Miyazaki et al. | |
| 7,939,540 B2 | 5/2011 | Miyazaki et al. | |
| 2006/0258703 A1 | 11/2006 | Shii et al. | |
| 2007/0299094 A1 | 12/2007 | Miyazaki et al. | |
| 2009/0062539 A1 | 3/2009 | Yamamoto et al. | |

FOREIGN PATENT DOCUMENTS

| | | |
|---|---|---|
| AU | 2007218725 B2 | 8/2007 |
| CA | 2306985 A1 | 4/1999 |
| CA | 2 537 573 A1 | 8/2007 |
| EP | 1052254 A1 | 11/2000 |
| EP | 2189450 A1 | 5/2010 |
| EP | 1 992 622 B1 | 7/2011 |
| EP | 2189450 B1 | 12/2011 |
| EP | 2 202 229 B1 | 3/2012 |
| JP | 5-17481 A | 1/1993 |
| JP | 8-165251 A | 6/1996 |
| JP | 11-209350 A | 8/1999 |
| JP | 2001-192385 A | 7/2001 |
| JP | 2001-520196 A | 10/2001 |
| JP | 2005-29541 A | 2/2005 |
| JP | 2005-47909 A | 2/2005 |
| JP | 2005-529930 A | 10/2005 |
| JP | 2005-537262 A | 12/2005 |
| JP | 4778550 B2 | 9/2011 |
| WO | WO-98/10767 A2 | 3/1998 |
| WO | WO-99/20280 A1 | 4/1999 |
| WO | WO 99/37622 * | 7/1999 |
| WO | WO-99/37622 A1 | 7/1999 |
| WO | WO-03/099278 A1 | 12/2003 |
| WO | WO-2004/006920 A1 | 1/2004 |
| WO | WO-2005/082865 A1 | 9/2005 |
| WO | WO-2006/093226 A1 | 9/2006 |
| WO | WO-2007/097317 A1 | 8/2007 |
| WO | WO-2008/099887 A1 | 8/2008 |

OTHER PUBLICATIONS

Second Office Action for Chinese Patent Application No. 200880005202.8, issued on Feb. 15, 2012.
Australian Amendment, dated Jul. 1, 2010, for Australian Patent Application No. 2008290000.
Australian Office Action, dated Feb. 14, 2012, for Application No. 2008290001.
Canadian Voluntary Amendment, dated Feb. 17, 2010, for Canadian Patent Application No. 2696727.
Chinese Amendment, dated Aug. 13, 2010, for Chinese Patent Application No. 200880022081.8, with English Translation.
Chinese Amendment, dated Dec. 25, 2009, for Chinese Patent Application No. 200880022081.8, with English translation.
Chinese Office Action, dated Jul. 13, 2011, for Chinese Patent Application No. 200880022081.8, with English translation.
Chinese Office Action, dated Sep. 29, 2011, for Chinese Patent Application No. 200880022081.8, with English translation.
European Amendments, dated Apr. 29, 2010, for European Patent Application No. 08827791.8.
European Office Action, dated Feb. 24, 2011, for European Patent Application No. 08827791.8.
European Office Action, dated Jul. 13, 2011, for European Patent Application No. 08827791.8.
European Office Action, dated Nov. 24, 2011, for European Patent Application No. 08827791.8.

(Continued)

Primary Examiner — Paul V. Ward
(74) Attorney, Agent, or Firm — Birch, Stewart, Kolasch & Birch, LLP (57) ABSTRACT

[4-(3-aminophenyl)-6,7-dimethoxyquinazolin-2-yl]methylamine with a favorable yield and high purity can be produced by subjecting a compound represented by the following formula (I) to a step of reacting with methylamine and a step of deprotection if desired:

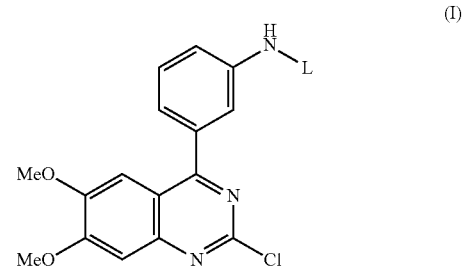

(I)

wherein L represents a protective group of amino.

8 Claims, 2 Drawing Sheets

OTHER PUBLICATIONS

European Office Action, dated Oct. 11, 2010, for European Patent Application No. 08827791.8.
Extended European Search Report, dated Sep. 22, 2010, for European Application No. 08827791.8.
Indian Voluntary Amendment, dated Mar. 15, 2010, for Indian Patent Application No. 1465/CHENP/2010.
Israel Office Action, dated Jun. 5, 2011, for Israel Patent Application No. 204017, with English translation.
Korean Amendment, dated Mar. 18, 2010, for Korean Patent Application No. 10-2009-7026235, with English translation.
Norwegian Office Action, dated Mar. 8, 2012, for Application No. 20083980, with English translation.
Reply to European Action, dated Nov. 10, 2010, for European Patent Application No. 08827791.8.
Reply to European Office Action, dated Mar. 17, 2011, for European Patent Application No. 08827791.8.
Reply to European Search Report, dated Oct. 19, 2010, for European Patent Application No. 08827791.8.
Response to Chinese Office Action, dated Nov. 24, 2011, for Chinese Patent Application No. 200880022081.8, with English translation.
Response to Chinese Office Action, dated Sep. 14, 2011, for Chinese Patent Application No. 200880022081.8, with English translation.
"The Fourth Series of Experimental Chemistry," vol. 1, Fundamental Procedure I, Edited by the Chemical Society of Japan, Maruzen Co. Ltd., 1990, pp. 184-186.
English translations of the Notification of Transmittal of the International Preliminary Report on Patentability (Form PCT/IB/338), International Preliminary Report on Patentability (Form PCT/IB/373), and Written Opinion of the International Searching Authority (Form PCT/ISA/237) issued Aug. 27, 2009, for PCT/JP2008/052448.
Greene et al., "Protective Groups in Organic Synthesis," Third Edition, Protection for the Amino Group, 1999, pp. 518-525, pp. 551-555.
Hanifin et al., Journal of Investigative Dermatology, vol. 107, No. 1, Jul. 1996, pp. 51-56.
Klein et al., Archives of Dermatology, vol. 135, Dec. 1999, pp. 1522-1525.
Leung et al., The Lancet, vol. 361, No. 9352, Jan. 11, 2003, pp. 151-160.
Yosipovitch et al., The Lancet, vol. 361, No. 9358, Feb. 22, 2003, pp. 690-694.
Schmidt, MD et al., "The phosphodiesterase 4 inhibitor roflumilast is effective in the treatment of allergic rhinitis," Journal of Allergy and Clinical Immunology, vol. 108, No. 4, 2001, pp. 530-0536.
English translations of the Notification of Transmittal of the International Preliminary Report on Patentability (Form PCT/IB/338), International Preliminary Report on Patentability (Form PCT/IB/373), Written Opinion of the International Searching Authority (Form PCT/ISA/237) issued Mar. 18, 2010 and International Search Report (Form PCT/ISA/210) issued Sep. 9, 2008 for International Application No. PCT/JP2008/064620.
International Search Report mailed Sep. 9, 2008 in International Application No. PCT/JP2008/064621.
Examination Response dated Apr. 23, 2012, for Australian Application No. 2008290000.
Repsonse to the Notice Prior to Examination dated Apr. 4, 2012, for Israeli Application No. 204017 with English translation.
Chinese Notice of Allowance, dated Jun. 6, 2012, for related Chinese Application No. 200880005202.8, with English translation.
Japanese Office Action dated Jun. 26, 2012, for Japanese Application No. 2008-558123.
U.S. Office Action dated Jun. 13, 2012, for U.S. Appl. No. 12/673,715.
Yakuji Nippo Limited, "Iyakuhin Tenkabutsu Jiten 2007" ("Pharmaceutical Excipients Dictionary 2007"), Edited by Japan Pharmaceutical Excipients Council, Jul. 25, 2007, pp. 280-282 and p. 309.
Yakuji Nippo Limited, "Iyakuhin Tenkabutsu Jiten 2007" ("Pharmaceutical Excipients Dictionary 2007"), Edited by Japan Pharmaceutical Excipients Council, Jul. 25, 2007, pp. 279-280.
International Preliminary Report on Patentability (Forms PCT/IB/338 and PCT/IB/373) and Written Opinion of the International Searching Authority (Form PCT/ISA/237), mailed Mar. 18, 2010, for International Application No. PCT/JP2008/064621.
Office Action dated Oct. 5, 2010 for U.S. Appl. No. 11/707,904.
Extended European Search Resort mailed Aug. 11, 2010 in Application No. 08827867.6.
Notice of Allowance for U.S. Appl. No. 12/032,550 issued on Feb. 13, 2012.
Australian Office Action, dated Feb. 13, 2012, for Australian Application No. 2008290000.
Notice of Acceptance for corresponding Australian Patent Application No. 200829000, dated May 1, 2012.
Chinese Notice of Allowance, dated May 4, 2012, for counterpart Chinese Application No. 200880022081.8, with English translation.
Japanese Office Action, dated May 15, 2012, for counterpart Japanese Application No. 2009-529019, with English translation.
Norwegian Office Action, dated May 7, 2012, for Application No. 20083980, with English translation.
Notice of Allowance for Canadian Patent Application No. 2,637,573, dated Nov. 23, 2012.
Office Action for Korean Patent Application No. 10-2008-7021869, dated Nov. 20, 2012.
Notice of Acceptance for Australian Patent Application No. 2008215411, dated Nov. 12, 2012.
Notice of Allowance for U.S. Appl. No. 12/673,715, dated Jan. 9, 2013.
Submission for Canadian Patent Application No. 2,637,573, dated Jan. 9, 2013.
Office Action for Taiwanese Patent Application No. 097131272, dated Dec. 20, 2012.
Office Action for Taiwanese Patent Application No. 096105966, dated Jan. 3, 2013.
Decision of Patent Grant for Japanese Patent Application No. 2009-529019, dated Jul. 31, 2012.
Notice of Reasons for Rejection for Japanese Patent Application No. 2008-558123, dated Jul. 31, 2012.
Office Action for Australian Patent Application No. 2008215411, dated May 31, 2012.
Australian Notice of Acceptance for Application No. 2008290001 dated Jul. 26, 2012.
Chinese Office Action for Application No. 200880022003.8 dated Jul. 4, 2012 (with English translation).
Decision of Patent Grant for corresponding Japanese Patent Application No. 2009-529018, mailed Jul. 10, 2012.
Notice of Allowance for Japanese Patent Application No. 2008-558123, dated Sep. 25, 2012.
Notice Prior to Allowance for corresponding Israeli Patent Application No. 204017, dated Sep. 19, 2012.
Notice of Allowance for Norwegian Patent Application No. 20083980, dated Nov. 14, 2012.
Notice of Deficiencies for Israeli Patent Application No. 193322, dated Oct. 28, 2012.
Notification to Grant Patent Right for Invention for Chinese Patent Application No. 200880022003.6, dated Jan. 17, 2013.
Notice of Allowance for U.S. Appl. No. 12/673,715, dated Apr. 18, 2013.
Office Action for Canadian Patent Application No. 2,678,477, dated Apr. 19, 2013.
Office Action for corresponding Canadian Patent Application No. 2,696,727, dated Mar. 21, 2013.

* cited by examiner

SEQUENCE LISTING

<160> NUMBER OF SEQ ID NOS: 10

<210> SEQ ID NO 1
<211> LENGTH: 25
<212> TYPE: DNA
<213> ORGANISM: Artificial
<220> FEATURE:
<223> OTHER INFORMATION: forward primer for CYP1A1: hCYP1A1_F1

<400> SEQUENCE: 1
tggtctccct tctctacact cttgt                                        25

<210> SEQ ID NO 2
<211> LENGTH: 31
<212> TYPE: DNA
<213> ORGANISM: Artificial
<220> FEATURE:
<223> OTHER INFORMATION: reverse primer for CYP1A1: hCYP1A1_R1

<400> SEQUENCE: 2
attttcccta ttacattaaa tcaatggttc t                                 31

<210> SEQ ID NO 3
<211> LENGTH: 21
<212> TYPE: DNA
<213> ORGANISM: Artificial
<220> FEATURE:
<223> OTHER INFORMATION: forward primer for CYP1A2: hCYP1A2_F_EJCP

<400> SEQUENCE: 3
gttcctgcag aaaacagtcc a                                            21

<210> SEQ ID NO 4
<211> LENGTH: 19
<212> TYPE: DNA
<213> ORGANISM: Artificial
<220> FEATURE:
<223> OTHER INFORMATION: reverse primer for CYP1A2: hCYP1A2_R_EJCP

<400> SEQUENCE: 4
ctgtgcttga acagggcac                                               19

<210> SEQ ID NO 5
<211> LENGTH: 33
<212> TYPE: DNA
<213> ORGANISM: Artificial
<220> FEATURE:
<223> OTHER INFORMATION: probe for CYP1A2: hCYP1A2_probe_EJCP

<400> SEQUENCE: 5
agcactatca ggactttgac aagaacagtg tct                               33

<210> SEQ ID NO 6
<211> LENGTH: 22
<212> TYPE: DNA
<213> ORGANISM: Artificial
<220> FEATURE:
<223> OTHER INFORMATION: forward primer for CYP3A4: hCYP3A4_F_m

<400> SEQUENCE: 6
gcaggaggaa attgatgcag tt                                           22

<210> SEQ ID NO 7
<211> LENGTH: 27
<212> TYPE: DNA
<213> ORGANISM: Artificial
<220> FEATURE:
<223> OTHER INFORMATION: reverse primer for CYP3A4: hCYP3A4_R_x

<400> SEQUENCE: 7
gtcaagatac tccatctgta gcacagt                                      27

<210> SEQ ID NO 8
<211> LENGTH: 27
<212> TYPE: DNA

```
<213> ORGANISM: Artificial
<220> FEATURE:
<223> OTHER INFORMATION: probe for CYP3A4: hCYP3A4_probe_m

<400> SEQUENCE: 8
acccaataag gcaccaccca cctatga                                      27

<210> SEQ ID NO 9
<211> LENGTH: 19
<212> TYPE: DNA
<213> ORGANISM: Artificial
<220> FEATURE:
<223> OTHER INFORMATION: forward primer for GAPDH: hGAPDH_F

<400> SEQUENCE: 9
gaaggtgaag gtcggagtc                                               19

<210> SEQ ID NO 10
<211> LENGTH: 20
<212> TYPE: DNA
<213> ORGANISM: Artificial
<220> FEATURE:
<223> OTHER INFORMATION: reverse primer for GAPDH: hGAPDH_R

<400> SEQUENCE: 10
gaagatggtg atgggatttc                                              20
```

METHOD FOR PRODUCING QUINAZOLINE DERIVATIVE

TECHNICAL FIELD

The present invention relates to a method for producing [4-(3-aminophenyl)-6,7-dimethoxyquinazolin-2-yl]methylamine and to an intermediate thereof.

BACKGROUND ART

Compounds having phosphodiesterase 4 (PDE4) inhibitory action have been expected to be useful for the treatment of allergic diseases such as atopic dermatitis. For example, Patent Document 1 discloses a compound having the following structural formula as a compound having PDE4 inhibitory action.

[Formula 1]

The aforementioned cound can be synthesized via [4-(3-aminophenyl)-6,7-dimethoxyquinazolin-2-yl]methylamine, and the method for synthesizing [4-(3-aminophenyl)-6,7-dimethoxyquinazolin-2-yl]methylamine disclosed in Patent Document 1 is as shown in the following scheme. That is to say, this compound is obtained via a compound having a nitro group, using 2,4-dichloro-6,7-dimethoxyquinazoline as the starting material.

[Formula 2]

[Patent Document 1] WO 99/37622

DISCLOSURE OF THE INVENTION

Problems to be Solved by the Invention

The present inventors have found methyl N-[3-(6,7-dimethoxy-2-methylaminoquinazolin-4-yl)phenyl]terephthalamic acid, etc. to be superior PDE4 inhibitors compared to the compound described in Patent Document 1. These compounds can be synthesized by coupling methyl 4-chlorocarbonylbenzoate with [4-(3-aminophenyl)-6,7-dimethoxyquinazolin-2-yl]methylamine. The aforementioned method for synthesizing [4-(3-aminophenyl)-6,7-dimethoxyquinazolin-2-yl]methylamine described in Patent Document 1 is not necessarily reasonable as an industrial production method from viewpoints that the synthesis is mediated by an explosive compound having a nitro group, purification by column chromatography is required, the overall yield is low, and the like.

Accordingly, an object of the present invention is to provide an industrially usable method for producing [4-(3-aminophenyl)-6,7-dimethoxyquinazolin-2-yl]methylamine. Furthermore, another object of the present invention is to provide intermediates that can be used in this production method.

Means for Solving the Problems

As a result of intensive studies, the present inventors have found the present invention. That is to say, the present invention provides the following [1] to [4]:

[1] a method for producing [4-(3-aminophenyl)-6,7-dimethoxyquinazolin-2-yl]methylamine, comprising subjecting a compound represented by the following formula (I):

wherein L represents a protective group of amino
to the following steps:
a step of reacting with methylamine; and
a step of deprotection if desired.

[2] the production method according to [1], wherein the compound represented by the formula (I):

wherein L represents a protective group of amino
is obtained by reacting 2,4-dichloro-6,7-dimethoxyquinazoline with a compound represented by the following formula (II):

wherein L represents a protective group of amino, and X represents —$B(OH)_2$, —$B(OR^1)(OR^2)$ where $R^1$ and $R^2$ each independently represent hydrogen or $C_{1-6}$ alkyl or $R^1$ and $R^2$ represent together dimethylmethylene, 1,2-ethylene, 1,3-propylene, or 2,3-dimethyl-butane-2,3-diyl, or —$BF_3M$ where M represents sodium or potassium.

[3] the production method according to [1] or [2], wherein L represents formyl, t-butoxycarbonyl, or acetyl.

[4] t—Butyl [3-(2-chloro-6,7-dimethoxyquinazolin-4-yl)phenyl]carbamate, N-[3-(2-chloro-6,7-dimethoxyquinazolin-4-yl)phenyl]formamide, or N-[3-(2-chloro-6,7-dimethoxyquinazolin-4-yl)phenyl]acetamide.

Effect of the Invention

The present invention has found an industrially usable method for producing [4-(3-aminophenyl)-6,7-dimethoxyquinazolin-2-yl]methylamine with a favorable yield and high purity. Furthermore, the present invention can provide a production intermediate that can be used in the aforementioned production method.

BEST MODE FOR CARRYING OUT THE INVENTION

The present production method is a method for producing [4-(3-aminophenyl)-6,7-dimethoxyquinazolin-2-yl]methylamine represented by the formula (III), comprising: step 1 of subjecting 2,4-dichloro-6,7-dimethoxyquinazoline represented by the formula (A-1) and a compound (II) acting as a boron metal reagent to a coupling reaction like Suzuki reaction, in an inert solvent, in the presence of a palladium(0) catalyst, under the atmosphere of inert gas or without such atmosphere, in the presence or absence of a base, and in the presence or absence of additives, so as to obtain a compound (I); then step 2 of converting the chloro group of the compound (I) to a methylamino group, so as to obtain a compound (A-3); and step 3 of deprotecting a protected amino group of the compound (A-3) if desired.

Step 2 of introducing a methylamino group and step 3 of deprotecting a protected amino group may be switched.

[Formula 6]

-continued (III)

wherein X represents —B(OH)$_2$, —B(OR$^1$)(OR$^2$) where R$^1$ and R$^2$ each independently represent hydrogen or C$_{1-6}$ alkyl or R$^1$ and R$^2$ represent together dimethylmethylene, 1,2-ethylene, 1,3-propylene, or 2,3-dimethyl-butane-2,3-diyl, or —BF$_3$M where M represents sodium or potassium, and L represents a protective group of amino.

<Step 1: Coupling Reaction>

This step is a step of reacting a compound (A-1) and a compound (II) in an inert solvent, in the presence of a palladium(0) catalyst, in the presence of a base, in the presence or absence of additives, and under the atmosphere of inert gas or without such atmosphere, so as to produce a compound (I).

As this step, a known coupling reaction of an aromatic boron compound (for example, a boron derivative such as boronic acid, boronic ester, borane, or trifluoroborate) and an aromatic halogen compound can be used. For example, refer to Miyaura B. N., Yanagi T., and Suzuki A., Synthetic Communications, 11 (1981), p. 513 ff.; Sharp M. J., Chen W., and Snieckus V., Tetrahedron Letters, 28 (1987), p. 5093 ff.; Gray G. W., J. Chem. Soc. Perkin Trans. II, 1989, p. 2041 ff., and Mol. Cryst. Sig. Cryst., 172 (1989), p. 165 ff., 204 (1991), p. 43 ff., and p. 91 ff.; EP0449015; WO89/12039; WO89/03821; and EP0354434.

Furthermore, this step can be carried out in accordance with the literature mentioned in Stanforth S. P., Tetrahedron (1998), 54, 263., Miyaura N. and Suzuki A., Chem. Rev. (1995), 95, 2457, etc. More specifically, this step can be carried out, referring to the reaction conditions, operations conducted after the reaction, a purification method, etc., which are described in Examples 1, 5, and 7 below.

2,4-Dichloro-6,7-dimethoxyquinazoline represented by the formula (A-1) is a known compound, and a commercially available product can be purchased and used.

The type of the compound (II) used herein for coupling is not particularly limited, as long as a compound of interest can be obtained and non-separable by-products are not generated, but X represents —B(OH)$_2$, —B(OR$^1$)(OR$^2$) where R$^1$ and R$^2$ each independently represent hydrogen or C$_{1-6}$ alkyl or R$^1$ and R$^2$ represent together dimethylmethylene, 1,2-ethylene, 1,3-propylene, or 2,3-dimethyl-butane-2,3-diyl, or —BF$_3$M where M represents sodium or potassium, and L represents a protective group of amino. Examples of the compound (II) may include 3-(N-t-butoxycarbonylamino)phenyl borate, 3-acetamidephenyl borate, or N-[3-(4,4,5,5-tetramethyl-1,3,2-dioxaborolan-2-yl)phenyl]formamide. A preferred example is N-[3-(4,4,5,5-tetramethyl-1,3,2-dioxaborolan-2-yl)phenyl]formamide or the like.

The term "C$_{1-6}$ alkyl" is used in the present specification to mean a linear or branched-chain alkyl group containing 1 to 6 carbon atoms. Specific examples of C$_{1-6}$ alkyl may include methyl, ethyl, 1-propyl (n-propyl), 2-propyl (i-propyl), 2-methyl-1-propyl (1-butyl), 2-methyl-2-propyl (t-butyl), 1-butyl (n-butyl), 2-butyl (s-butyl), 1-pentyl, 2-pentyl, 3-pentyl, 2-methyl-1-butyl, 3-methyl-1-butyl, 2-methyl-2-butyl, 3-methyl-2-butyl, 2,2,-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl 2,3-dimethyl-2-butyl or the like.

Preferred examples may include C$_{1-3}$ alkyl such as methyl, ethyl, 1-propyl (n-propyl), 2-propyl (i-propyl), 2-methyl-1-propyl (1-butyl), 2-methyl-2-propyl (t-butyl), 1-butyl (n-butyl), or 2-butyl (s-butyl). More preferred examples may include methyl and ethyl.

The compound (II) can be used in an amount of 0.5 to 10 times, and preferably 0.5 to 1.5 times the molar equivalent of the compound (A-1).

The type of a solvent used herein is not particularly limited, as long as it dissolves starting substances to a certain extent and does not inhibit the reaction of this step. Specific examples of such a solvent may include: amides such as formamide, dimethylformamide, dimethylacetamide, hexamethylphosphoric acid triamide, or N-methylpyrrolidone; aromatic hydrocarbons such as toluene, benzene, xylene, or mesitylene; ethers such as diethyl ether, diisopropyl ether, tetrahydrofuran, dioxane, dimethoxyethane, or diethylene glycol dimethyl ether; alcohols such as methanol, ethanol, n-propanol, isopropanol, n-butanol, isobutanol, t-butanol, isoamyl alcohol, diethylene glycol, glycerine, octanol, cyclohexanol, or methyl cellosolve; nitriles such as acetonitrile or isobutyronitrile; sulfoxides such as dimethyl sulfoxide or sulfolane; esters such as methyl acetate, ethyl acetate, propyl acetate, or diethyl carbonate; water; and a mixture of these solvents. Preferred examples are toluene, tetrahydrofuran, ethyl acetate, or water, or a mixture of these solvents.

The type of a palladium(0) catalyst used herein is not particularly limited, as long as a compound of interest can be obtained and non-separable by-products are not generated. Examples of such a palladium(0) catalyst may include tetrakis(triphenylphosphine)palladium, tris(dibenzylideneacetone)dipalladium, bis(dibenzylideneacetone)palladium, bis(tri-t-butylphosphine)palladium, palladium black, various types of palladium complexes that become palladium(0) precursors as described below, or a palladium(0) catalyst generated in a reaction system as a result of combination with various types of ligands as described below.

That is to say, the types of various types of palladium complexes that become palladium(0) precursors are not particularly limited, as long as a compound of interest can be obtained and non-separable by-products are not generated. Specific examples of such palladium complexes may include palladium acetate, 1,1'-bis(diphenylphosphino)ferrocene dichloropalladium, dichlorobis(tri-o-tolylphosphine)palladium, or dichlorobis(tris cyclohexylphosphine)palladium. The type of a ligand is not particularly limited, as long as a compound of interest can be obtained and non-separable by-products are not generated. Specific examples of such a ligand may include 2,2'-bis(diphenylphosphino)-1,1'-binaphthyl (BINAP), 9,9-dimethyl-4,5-bis(diphenylphosphino)xanthene (Xantphos), tri-t-butylphosphine, tri(4-methylphenyl)phosphine, tri-2-furylphosphine, 2-(di-t-butylphosphino)biphenyl, 2-(dicyclohexylphosphino)biphenyl, tricyclohexylphosphine, 2-dicyclohexylphosphino 2'-(N,N-dimethylamino)biphenyl, 1,1'-bis(diphenylphosphino)ferrocene, di-t-butylphosphonium tetrafluoroborate, 1,3-bis(2,4,6-trimethylphenyl)imidazole-2-ylidene or the like.

The aforementioned palladium(0) catalyst can be used in an amount of 0.01 to 5 times, and preferably 0.01 to 0.1 times the molar equivalent of the compound (A-1).

The type of a base used herein is not particularly limited, as long as a compound of interest can be obtained and non-separable by-products are not generated. Specific examples of such a base may include: inorganic bases such as tripotassium phosphate, trisodium phosphate, cesium carbonate, potassium carbonate, sodium carbonate, cesium hydrogencarbonate, potassium hydrogencarbonate, sodium hydrogencarbonate, sodium acetate, barium hydroxide, potassium hydroxide, potassium fluoride, or cesium fluoride; metal alkoxides such as sodium ethoxide or sodium-t-butoxide; acetates of alkali metals such as sodium acetate or potassium acetate; organic bases such as triethylamine or the like. Preferred examples are potassium carbonate or sodium carbonate.

The aforementioned base can be used in an amount of 1 to 100 times, and preferably 1 to 20 times the molar equivalent of the compound (A-1).

The type of an additive used herein is not particularly limited, as long as a compound of interest can be obtained and non-separable by-products are not generated. Specific examples of such an additive may include lithium chloride, sodium chloride, lithium bromide, sodium bromide, tetrabutylammonium bromide or the like.

The aforementioned additive can be used in an amount of 1 to 100 times, and preferably 1 to 10 times the molar equivalent of the compound (A-1).

The reaction temperature is not particularly limited. It is generally between −30° C. and 180° C., and preferably between 0° C. and 100° C.

The reaction time is not particularly limited. It is generally between 0.5 and 200 hours, and preferably between 1 and 100 hours.

When the reaction is carried out under the atmosphere of inert gas, the type of such inert gas is not particularly limited unless it inhibits the reaction in this step. Specific examples may include argon or nitrogen.

As a protective group of amino, a protective group known to those skilled in the art can be used. Preferred examples of a protective group include cyclic imide protective groups, amide protective groups, or carbamate protective groups. More preferred examples are formyl, t-butoxycarbonyl, or acetyl.

This step can be further carried out by cross coupling of a metallated aryl and an aromatic halide, for example, a Grignard reagent or an organic lithium reagent [for example, refer to Fauvarque J. F. and Jutard A., Bull. Chim. Soc. Fr., 1976, 765; Sekiya A. and Ishikawa N., J. Organomet. Chem., 1976, 118, 349; Sekiya A. and Ishikawa N., J. Organomet. Chem., 1977, 125, 281; Yamamura M., Monitani I., and Murahashi S. I., J. Organomet. Chem., 1975, 91, C39; Murahashi S. I., Yamamura M., Yanagisawa K., Mita N., and Kondo K., J. Org. Chem., 1979, 44, 2408; and Minato A., Tamano K., Hayashi T., Suzuki K., and Kumada M., Tetrahedron Lett., 1980, 845], organic zinc reagents [for example, refer to Negishi E. et al., J. Org. Chem., 42 (1977), 1822], organic tin reagents [for example, refer to Kosugi M. et al., Chem. Lett. 1977, 301; Stille J. K., Angew. Chem. Int. Ed. Engl., 25, 508, 1986; and Mitchell T. N., Synthesis, 803, 1992], and organic silicon reagents [for example, refer to Hiyama T. et al., J. Org. Chem., 1996, 61, 7232].

<Step 2>

This step is a step of reacting the compound (I) and methylamine in an inert solvent to obtain a compound (A-3).

Methylamine can be used in an amount of 1 to 200 times, and preferably 1 to 40 times the molar equivalent of the compound (I).

The type of a solvent used herein is not particularly limited, as long as it dissolves starting substances to a certain extent and it does not inhibit the reaction in this step. Examples of such a solvent may include: aromatic hydrocarbons such as toluene, benzene, or xylene; ethers such as diethyl ether, tetrahydrofuran, dimethoxyethane, or dioxane; alcohols such as methanol, ethanol, n-propanol, isopropanol, n-butanol, t-butanol, or ethylene glycol; water; and a mixture of these solvents. A preferred example is a mixed solvent of isopropanol or methanol and tetrahydrofuran.

The method of adding methylamine used herein is not particularly limited, as long as a compound of interest can be obtained and non-separable by-products are not generated. For example, methylamine can be added in the form of gas, a solution in methanol, ethanol, tetrahydrofuran, water, or the like, or a salt such as hydrochloride. Methylamine is preferably added as a solution in methanol.

The reaction temperature is not particularly limited. It is generally between −30° C. and 180° C., and preferably between 0° C. and 150° C.

The reaction time is not particularly limited. It is generally between 0.5 and 200 hours, and preferably between 1 and 100 hours.

In this step, in general, a hermetically sealed reactor that is resistant to pressure, such as a stainless steel reactor, is used.

<Step 3>

This step is a step of deprotecting a protected amino group of the compound (A-3) if desired. As this step, a known deprotection reaction can be used. For example, the amino group can be deprotected by the methods described in Synthesis, pp. 66-68, 1999 and the like when a protective group is t-butoxycarbonyl, the methods described in J. Am. Chem. Soc., pp. 1154, 1958; J. Org. Chem., pp. 3748, 1979; and the like when a protective group is formyl, and the methods described in J. Org. Chem., pp. 4593, 1978 and the like when a protective group is acetyl.

The type of a reaction solvent used herein is not particularly limited, as long as it dissolves starting substances to a certain extent and it does not inhibit the reaction in this step. Examples of such a reaction solvent may include: aromatic hydrocarbons such as toluene, benzene, or xylene; ethers such as diethyl ether, tetrahydrofuran, dimethoxyethane, or dioxane; alcohols such as methanol, ethanol, n-propanol, isopropanol, n-butanol, t-butanol, or ethylene glycol; halogen solvents such as dichloromethane or dichloroethane; water; and a mixture of these solvents. Preferred examples are methanol, ethanol, or dichloromethane.

The type of an acid used herein is not particularly limited, as long as it promotes a reaction. Examples of such an acid may include: mineral acids such as hydrochloric acid or sulfuric acid; and organic acids such as formic acid, acetic acid, or trifluoroacetic acid. Preferred examples are hydrochloric acid, sulfuric acid, and trifluoroacetic acid.

The type of a base used herein is not particularly limited, as long as it promotes a reaction. Examples of such a base may include: inorganic bases such as sodium hydroxide or potassium hydroxide and organic bases such as hydrazine or alkyl amine.

The reaction temperature is not particularly limited. It is generally between −30° C. and 180° C., and preferably between 0° C. and 100° C.

The reaction time is not particularly limited. It is generally between 0.5 and 200 hours, and preferably between 1 and 100 hours.

The compound (III) obtained in the present invention can be used to produce a compound (IV), which is a compound having PDE4 inhibitory action (see step 4 described below).

[Formula 7]

wherein R represents $C_{1-6}$ alkyl.

<Step 4>

This step is a method of reacting [4-(3-aminophenyl)-6,7-dimethoxyquinazolin-2-yl]methylamine represented by the formula (III) and a compound (B-2), which is an acid chloride, in an inert solvent, in the presence of or in the absence of a base to produce the compound (IV).

The compound (B-2) is a known compound and can be easily obtained.

The compound (B-2) can be used in an amount of 1 to 10 times, and preferably 1 to 2 times the molar equivalent of the compound (III).

The type of a solvent used herein is not particularly limited, as long as it dissolves starting substances to a certain extent and it does not inhibit the reaction in this step. Examples of such a solvent may include: amides such as formamide, dimethylformamide, dimethylacetamide, hexamethylphosphoric acid triamide, or N-methylpyrrolidone; aromatic hydrocarbons such as toluene, benzene, or xylene; ethers such as diethyl ether, tetrahydrofuran, dimethoxyethane, or dioxane; halogenated hydrocarbons such as dichloromethane, chloroform, 1,2-dichloroethane, or carbon tetrachloride; organic bases such as pyridine or 2-, 3- or 4-picoline; water; and a mixture of these solvents. Preferred examples are dimethylacetamide, tetrahydrofuran, or pyridine.

The type of a base used herein is not particularly limited, as long as a compound of interest can be obtained and non-separable by-products are not generated. Examples of such a base may include: inorganic bases such as sodium carbonate, potassium carbonate, sodium hydrogencarbonate, potassium hydrogencarbonate, or cesium carbonate and organic bases such as pyridine, triethylamine, or diisopropylethylamine. Preferred examples are pyridine or diisopropylethylamine.

The aforementioned base can be used in an amount of 1 to 10 times, and preferably 1 to 4 times the molar equivalent of the compound (III).

The reaction temperature varies depending on the solvent and reagent. It is generally between −30° C. and 180° C., and preferably between 0° C. and 100° C., and within the boiling point range of the solvent.

The reaction time varies depending on the solvent and reaction temperature. It is generally between 0.5 and 200 hours, and preferably between 1 and 100 hours.

EXAMPLES

The compound of the present invention can be produced by the methods described in the following examples. However, these examples are provided for illustrative purposes only. Specific examples as described below are not intended to limit the scope of the invention in any case. In addition, various modifications may also be made within the scope of the present invention.

Compounds, to which publication names or the like are attached, were produced in accordance with the publications or the like.

Example 1

Synthesis of t-butyl [3-(2-chloro-6,7-dimethoxyquinazolin-4-yl)phenyl]carbamate

[Formula 8]

To a mixture of 1.00 g (3.86 mmol) of 2,4-dichloro-6,7-dimethoxyquinazoline, 1.14 g (4.63 mmol) of 3-(N-t-butoxycarbonylamino)phenyl borate, tetrahydrofuran (25 mL), and 2 M sodium carbonate aqueous solution (5 mL) were added palladium acetate (8.84 mg) and 1,1'-bis(diphenylphosphino)ferrocene (21.4 mg) in this order, and the mixture was stirred at 60° C. for 6.5 hours under a nitrogen atmosphere. The reaction mixture was allowed to cool, and ethyl acetate (25 mL) and 5% w/w sodium chloride solution (20 mL) were added to extract the organic layer. The organic layer was washed twice with 5% w/w sodium chloride solution (20 mL) and then concentrated under reduced pressure. To the concentration residue were added ethyl acetate (1 mL) and 2-propanol (4 mL), and the mixture was suspended by stirring at 40° C. for 0.5 hours. The suspension was cooled, and the precipitated crystals were collected by filtration and dried to give 1.48 g of a target product (yield: 91.5%).

¹H-NMR. (CDCl₃) δ (ppm): 1.52 (9H, s), 3.97 (3H, s), 4.07 (3H, s), 6.62 (1H, br), 7.33 (1H, s), 7.38-7.43 (1H, m), 7.48-7.53 (3H, m), 8.00 (1H, br). ESI MS: m/z 438 (M+Na)⁺.

Example 2

Synthesis of 3-(2-chlro-6,7-dimethoxy-quinazolin-4-yl)phenylamine

[Formula 9]

Under a nitrogen atmosphere, 420 mg (1.00 mmol) of t-butyl [3-(2-chloro-6,7-dimethoxyquinazolin-4-yl)phenyl]carbamate was allowed to cool down to 5° C., trifluoroacetic acid (1 mL) was added dropwise while stirring, and the mixture was stirred at room temperature. The mixture was stirred for 1.25 hours, then allowed to cool down to 5° C. to 10° C., 2 N aqueous sodium hydroxide solution (6.2 mL) was added dropwise to precipitate pale yellow crystals. The mixture was stirred at room temperature for 15 minutes, and the precipitated crystals were filtration and dried to give 306 mg of a target product (yield: 95.6%).

¹H-NMR (DMSO-d₆) δ (ppm): 3.86 (3H, s), 4.01 (3H, s), 5.40 (2H, br), 6.79 (1H, dd, J=1.6, 8.0 Hz), 6.93 (1H, brd, J=8.0 Hz), 7.02 (1H, t, J=1.6 Hz), 7.24 (1H, t, J=8.0 Hz), 7.41 (1H, s), 7.43 (1H, s).

Example 3

Synthesis of t-butyl {3-[6,7-dimethoxy-2-(methylamino)quinazolin-4-yl]phenyl}carbamate

[Formula 10]

In a SUS autoclave were placed 420 mg (1.00 mmol) of t-butyl [3-(2-chloro-6,7-dimethoxyquinazolin-4-yl)phenyl]carbamate, tetrahydrofuran (2.5 mL), and 2-propanol (1.25 mL), to this mixture was added a methanol solution (2.5 mL) of 40% methylamine, and the mixture was stirred at 90° C. for 8 hours. The reaction mixture was allowed to cool and then poured into a mixed solution of ethyl acetate (40 mL), tetrahydrofuran (40 mL), and 5% w/w sodium chloride solution (50 mL) to extract the organic layer. The organic layer was washed with 5% w/w sodium chloride solution (50 mL) and then concentrated under reduced pressure. To the concentration residue was added t-butyl methyl ether (2.1 mL), and the mixture was crystallized with a spatula and then stirred at room temperature for 3 hours. The precipitated crystals were collected by filtration and dried to give 348 mg of a target product (yield: 83.8%).

¹H-NMR (CDCl₃) δ (ppm): 1.52 (9H, s), 3.12 (3H, d, J=5.2 Hz), 3.85 (3H, s), 4.03 (3H, s), 5.11 (1H, brd, J=5.2 Hz), 6.59 (1H, br), 7.07 (1H, s), 7.19 (1H, s), 7.36-7.48 (3H, m), 7.80 (1H, br). ESI MS: m/z 433 (M+Na)⁺.

Example 4

Synthesis of [4-(3-aminophenyl)-6,7-dimethoxyquinazolin-2-yl]methylamine

[Formula 11]

Under a nitrogen atmosphere, 100 mg (0.24 mmol) of t-butyl {3-[6,7-dimethoxy-2-(methylamino)quinazolin-4-yl]phenyl}carbamate was suspended in dichloromethane (1 mL), to the suspension was dropwise added trifluoroacetic acid (0.2 mL) while cooling to 0° C., the mixture was stirred at the same temperature for 1 hour followed by stirring at room temperature for 6 hours. While cooling with ice water, 0.5 N aqueous sodium hydroxide solution (5.94 mL) was added dropwise, and into the reaction mixture were poured ethyl acetate (10 mL), tetrahydrofuran (10 mL), and 5% w/w sodium chloride solution (20 mL) to extract the organic layer. The organic layer was washed twice with 5% w/w sodium chloride solution (20 mL) and then concentrated under reduced pressure. To the concentration residue was added t-butyl methyl ether (0.6 mL), and the mixture was crystallized with a spatula and stirred at room temperature for 4 hours. The precipitated crystals were collected by filtration and dried to give 66.1 mg of a target product (yield: 87.2%).

¹H-NMR (CDCl₃) δ (ppm): 3.12 (3H, d, J=5.2 Hz), 3.80 (2H, brs), 3.82 (3H, s), 4.03 (3H, s), 5.30 (1H, br), 6.83 (1H, dd, J=1.6, 8.0 Hz), 6.99 (1H, t, J=1.6 Hz), 7.04 (1H, brd, J=8.0 Hz), 7.07 (1H, s), 7.15 (1H, s), 7.30 (1H, t, J=8.0 Hz).

Example 5

Synthesis of N-[3-(2-chloro-6,7-dimethoxyquinazolin-4-yl)phenyl]formamide

[Formula 12]

To a mixture of 2.00 g (7.72 mmol) of 2,4-dichloro-6,7-dimethoxyquinazoline, 2.38 g (9.26 mmol) of N-[3-(4,4,5,5-tetramethyl-1,3,2-dioxaborolan-2-yl)phenyl]formamide, tetrahydrofuran (50 mL), and 2 M aqueous sodium carbonate solution (10 mL) were added palladium acetate (17.7 mg) and 1,1'-bis(diphenylphosphino)ferrocene (42.8 mg) in this order, and the mixture was stirred at 60° C. for 6 hours. The mixture was allowed to cool, then 5% w/w sodium chloride solution (50 mL) and ethyl acetate (50 mL) were added followed by stirring for 5 minutes, and the insoluble matter was collected by filtration. The filtrate was transferred to a separatory funnel to extract the organic layer. The organic layer was washed twice with 5% w/w sodium chloride solution (50 mL) and then concentrated under reduced pressure. To the concentration residue were added 2-propanol (15 mL) and ethyl acetate (10 mL), and the mixture was suspended by stirring at 50° C. for 2 hours. The suspension was allowed to cool, and then the precipitated crystals were collected by filtration and dried to give 667 mg of a target product. Meanwhile, the insoluble matter collected by filtration was dissolved in a mixed solution of dichloromethane/methanol (300 mL/100 mL), the mixture was filtered to remove the insoluble matter, and the filtrate was concentrated under reduced pressure. To the concentration residue were added 2-propanol (15 mL) and ethyl acetate (10 mL), and the mixture was suspended by stirring at 50° C. for 2 hours. The mixture was allowed to cool, and then the precipitated crystals were collected by filtration and dried to give 1.78 g of a target product. A total of 2.45 g was yielded, and the yield was 91.3%.

$^1$H-NMR (DMSO-$d_6$) δ (ppm): 3.86 (3H, s), 4.00 (3H, s), 7.41 (1H, s), 7.44 (1H, s), 7.45-7.60 (3H, m), 7.68-7.73 (1H, m), 8.14-8.18 (1H, m), 8.34 (1H, s), 10.47 (1H, br). ESI MS: m/z 366 (M+Na)$^+$.

Example 6

Synthesis of [4-(3-aminophenyl)-6,7-dimethoxyquinazolin-2-yl]methylamine

[Formula 13]

To 354 mg (1.00 mmol) of N-[3-(2-chloro-6,7-dimethoxyquinazolin-4-yl)phenyl]formamide, tetrahydrofuran (2.06 mL), and methanol (1.03 mL) was added a methanol solution (2.06 mL) of 40% methylamine, and the mixture was reacted at 90° C. for 12 hours. The reaction mixture was allowed to cool and then poured into a mixed solution of ethyl acetate (30 mL), tetrahydrofuran (30 mL), and 5% w/w sodium chloride solution (30 mL) to extract the organic layer. The organic layer was washed with 5% w/w sodium chloride solution (30 mL) and then concentrated under reduced pressure. To the concentration residue was added ethyl acetate (1.5 mL), and the mixture was crystallized with a spatula followed by stirring at 50° C. for 1.5 hours. To this suspension was dropwise added t-butyl methyl ether (1.5 mL), and the mixture was further stirred for 1 hour and allowed to cool gradually. The precipitated crystals were collected by filtration and dried to give 288 mg of a target product (yield: 90.5%).

$^1$H-NMR (CDCl$_3$) δ (ppm): 3.12 (3H, d, J=5.2 Hz), 3.80 (2H, brs), 3.82 (3H, s), 4.03 (3H, s), 5.30 (1H, br), 6.83 (1H, dd, J=1.6, 8.0 Hz), 6.99 (1H, t, J=1.6 Hz), 7.04 (1H, brd, J=8.0 Hz), 7.07 (1H, s), 7.15 (1H, s), 7.30 (1H, t, J=8.0 Hz).

Example 7

Synthesis of N-[3-(2-chloro-6,7-dimethoxyquinazolin-4-yl)phenyl]acetamide

[Formula 14]

To a mixture of 2.00 g (7.72 mmol) of 2,4-dichloro-6,7-dimethoxyquinazoline, 1.69 g (9.26 mmol) of 3-acetamidephenyl borate, tetrahydrofuran (50 mL), and 2 M aqueous sodium carbonate solution (10 mL) were added palladium acetate (17.7 mg) and 1,1'-bis(diphenylphosphino)ferrocene (42.8 mg) in this order under a nitrogen atmosphere, and the mixture was stirred at 60° C. for 5 hours. The mixture was allowed to cool, and then 5% w/w sodium chloride solution (50 mL) was added to the mixture followed by stirring for 1 hour. The mixture was filtered to remove the insoluble matter and rinsed with water (50 mL) and ethyl acetate (50 mL). The filtrate was transferred to a separatory funnel to extract the organic layer. The organic layer was washed twice with 5% w/w sodium chloride solution (50 mL) and then concentrated under reduced pressure. To the concentration residue were added 2-propanol (6 mL) and ethyl acetate (4 mL), and the mixture was suspended by stirring at 50° C. for 2 hours. The mixture was allowed to cool, and the precipitated crystals were collected by filtration and dried to give 471 mg of a target product. Furthermore, the insoluble matter collected by filtration was dissolved in dichloromethane/methanol (3/1) (50 mL), and the mixture was filtered to remove the insoluble matter. The filtrate was concentrated under reduced pressure, to the concentration residue were added 2-propanol (15 mL) and ethyl acetate (10 mL), and the mixture was suspended by stirring at 50° C. for 1.5 hours and allowed to cool gradually. The precipitated crystals were collected by filtration and dried to give 2.02 g of a target product. A total of 2.50 g was yielded, and the yield was 89.4%.

$^1$H-NMR (CDCl$_3$) δ (ppm): 2.21 (3H, s), 3.97 (3H, s), 4.07 (3H, s), 7.33 (1H, s), 7.37 (1H, br), 7.47 (1H, s), 7.49-7.59 (3H, m), 8.03 (1H, br). ESI MS: m/z 380 (M+Na)$^+$.

Example 8

Synthesis of N-{3-[6,7-dimethoxy-2-(methylamino)quinazolin-4-yl]phenyl}acetamide

[Formula 15]

To 353 mg (0.96 mmol) of N-[3-(2-chloro-6,7-dimethoxyquinazolin-4-yl)phenyl]acetamide, tetrahydrofuran (2.06 mL), and methanol (1.03 mL) was added a methanol solution (2.06 mL) of 40% methylamine, and the mixture was reacted at 90° C. for 9 hours. The mixture was allowed to cool and then poured into a mixed solution of ethyl acetate (30 mL) and 5% w/w sodium chloride solution (30 mL) while washing with tetrahydrofuran (30 mL) to extract the organic layer. The organic layer was washed with 5% w/w sodium chloride solution (30 mL) and then concentrated under reduced pressure. To the concentration residue was added t-butyl methyl ether (3 mL), and the mixture was crystallized with a spatula and then suspended by stirring at 50° C. for 2 hours. The mixture was allowed to cool gradually, and then the precipitated crystals were collected by filtration and dried to give 318 mg of a target product (yield: 91.1%).

$^1$H-NMR (CDCl$_3$) δ (ppm): 2.20 (3H, s), 3.12 (3H, d, J=4.8 Hz), 3.85 (3H, s), 4.03 (3H, s), 5.11 (1H, brd, J=4.8 Hz), 7.07 (1H, s), 7.18 (1H, s), 7.30 (1H, br), 7.43-7.52 (2H, m), 7.60-7.65 (1H, m), 7.85 (1H, br). ESI MS: m/z 375 (M+Na)$^+$.

Example 9

Synthesis of [4-(3-aminophenyl)-6,7-dimethoxyquinazolin-2-yl]methylamine

[Formula 16]

To a methanol (1.5 mL) solution of 100 mg (0.275 mmol) of N-{3-[6,7-dimethoxy-2-(methylamino)quinazolin-4-yl]phenyl}acetamide was added concentrated hydrochloric acid (0.5 mL), and the mixture was stirred at 50° C. Two hours later, methanol (1.5 mL) and concentrated hydrochloric acid (0.5 mL) were added, and the reaction was continued. Concentrated hydrochloric acid (0.5 mL) was added 0.5 hours later, and the reaction was continued. Two hours later, the heat source was switched off, and the mixture was stirred overnight. On the following day, methanol (3.0 mL) and concentrated hydrochloric acid (1.5 mL) were added, and the mixture was stirred at 50° C. for 4.5 hours. The mixture was allowed to cool down to room temperature, and the reaction mixture was allowed to cool in an ice water bath and neutralized with 5 N aqueous sodium hydroxide solution. The mixture was concentrated under reduced pressure, then to the concentration residue was added tetrahydrofuran (25 mL), and the mixture was poured into 5% w/w sodium chloride solution (25 mL) to extract the organic layer while washing with ethyl acetate (25 mL). The organic layer was washed twice with 5% w/w sodium chloride solution (25 mL) and then concentrated under reduced pressure. To the concentration residue was added t-butyl methyl ether (1 mL), and the mixture was stirred overnight at room temperature. The precipitated crystals were collected by filtration and dried to give 730 mg of a target product (yield: 83.3%).

$^1$H-NMR (CDCl$_3$) δ (ppm): 3.12 (3H, d, J=5.2 Hz), 3.80 (2H, brs), 3.82 (3H, s), 4.03 (3H, s), 5.30 (1H, br), 6.83 (1H, dd, J=1.6, 8.0 Hz), 6.99 (1H, t, J=1.6 Hz), 7.04 (1H, brd, J=8.0 Hz), 7.07 (1H, s), 7.15 (1H, s), 7.30 (1H, t, J=8.0 Hz).

Example 10

Synthesis of methyl N-[3-(6,7-dimethoxy-2-methylaminoquinazolin-4-yl)phenyl]terephthalamic acid

[Formula 17]

To a solution of 16.8 g of [4-(3-aminophenyl)-6,7-dimethoxyquinazolin-2-yl]methylamine and 8.6 g of pyridine dissolved in 300 mL of tetrahydrofuran was added 11.8 g of 4-chlorocarbonylbenzoic acid methyl ester at room temperature, followed by stirring for 24 hours. To the reaction mixture was added 100 mL of dimethyl sulfoxide, the mixture was partitioned between a mixed solvent consisting of 2,000 mL of ethyl acetate and 1,000 mL of tetrahydrofuran, and 1,000 mL of a saturated sodium hydrogencarbonate solution, and the organic layer was separated. The water layer was further extracted with a mixed solvent consisting of 500 mL of ethyl acetate and 500 mL of tetrahydrofuran. The combined organic layer was then washed with 1,000 mL of a saturated sodium hydrogencarbonate solution and 1,000 mL of brine in this order, and dried over anhydrous magnesium sulfate. The desiccant was removed by filtration with 100 g of a basic silica gel pad, followed by well washing with 2,000 mL of ethyl acetate. The combined eluent was concentrated under reduced pressure, and the obtained crude product was suspended and triturated in a mixed solvent consisting of 100 mL of tetrahydrofuran and 500 mL of diethyl ether. The precipitated crystals were collected by filtration, washed twice with 100 mL of diethyl ether, and dried under aeration at 50° C. for 5 hours to give 13.8 g of the crystals of the titled compound (yield: 53.2%).

$^1$H-NMR (DMSO-$d_6$) δ (ppm): 2.88 (3H, d, J=4.4 Hz), 3.74 (3H, s), 3.89 (3H, s), 3.92 (3H, s), 6.99 (1H, s), 7.00 (1H, brs), 7.17 (1H, s), 7.46 (1H, d, J=8.0 Hz), 7.55 (1H, t, J=8.0 Hz), 7.87 (1H, brd, J=8.0 Hz), 8.08 (4H, s), 8.20 (1H, brs), 10.61 (1H, s).

Example 11

Synthesis of methyl N-[3-(6,7-dimethoxy-2-methylaminoquinazolin-4-yl)phenyl]terephthalamic acid

[Formula 18]

(1) Preparation of "Terephthalic Acid Monomethyl Ester Chloride/N,N-Diisopropylethylamine" Solution A suspension of 1.997 kg (11.08 mol) of terephthalic acid monomethyl ester in 15.60 kg of 1,2-dimethoxyethane was stirred in a nitrogen atmosphere while being cooled at 10° C. To the suspension was added 400 mL (5.17 mol) of N,N-dimethylformamide and 1.323 kg (10.56 mol) of thionyl chloride in this order, and then the container was washed with 1.00 L of 1,2-dimethoxyethane. The suspension was stirred under heating at 60 to 73° C. for 1 hour and 2 minutes and then stirred while being cooled. 1.36 kg (10.52 mol) of N,N-diisopropylethylamine was added dropwise to the solution while cooling at 0° C., and the container was washed with 1.00 L of 1,2-dimethoxyethane. Then the reaction solution was stirred at 25° C., and the stirring was stopped 38 minutes after the internal temperature had reached 20° C. The reaction mixture was transferred into a plastic container, and 22.00 kg of "monomethyl terephthalate chloride/N,N-diisopropylethylamine" solution (terephthalic acid monomethyl ester chloride content: 1.84 kg) was obtained as a slightly tannish solution.

(2) Synthesis of methyl N-[3-(6,7-dimethoxy-2-methylaminoquinazolin-4-yl)phenyl]terephthalamic acid A suspension of 2.000 kg (6.39 mol) of [4-(3-aminophenyl)-6,7-dimethoxyquinazolin-2-yl]methylamine in 71.14 kg of tetrahydrofuran was stirred in a nitrogen atmosphere while being cooled at 0° C. To the suspension was added dropwise 16.70 kg of "monomethyl terephthalate chloride/N,N-diisopropylethylamine" solution (monomethyl terephthalate chloride content: 1.40 kg, 7.03 mol) over 1 hour and 26 minutes, and the container was washed with 1.40 L of 1,2-dimethoxyethane. The mixture was stirred at 0° C. for 13 hours and 4 minutes. Under cooling at 0° C., 36.5 kg of ethyl acetate was added to the reaction mixture and then 80.1 kg of a 5% aqueous solution of sodium hydrogencarbonate was added dropwise, and the mixture was stirred at 20° C. for 1 hour and 10 minutes. Then, 37.3 kg of ethyl acetate was added into the mixture, the mixture was stirred, and the water layer was separated. The organic layer was washed with 40.0 kg of a 5% aqueous solution of sodium chloride, 40.2 kg of water, and 40.1 kg of water in this order. The organic layer was concentrated under reduced pressure at a jacket temperature of 40° C., 23.70 kg of methanol was added to the residue, and stirred for 1 hour and 1 minute while being heated to 60 to 66° C. 23.60 kg of 2-propanol was added dropwise to the suspension over 1 hour while stirring the suspension at a jacket temperature of 50° C. Then, the suspension was cooled at a cooling rate of 10° C./hour and stirred at 20° C. for 12 hours and 23 minutes. The precipitated crystals were filtered, rinsed with a mixed solution of 3.00 L of methanol and 3.00 L of 2-propanol and 6.00 L of 2-propanol in this order to yield 5.52 kg of a crude product (content of the target compound: 2.57 kg, 5.44 mol) as pale yellow crystals (yield: 85.3%).

In a nitrogen atmosphere, a suspension of 5.398 kg of the crude product (content of the target compound: 2.518 kg, 5.33 mol) in 8.01 L of dimethyl sulfoxide was stirred under heating at 60 to 70° C., and the crystals were dissolved. The solution was filtered, and rinsed with 2.00 L of dimethyl sulfoxide. The filtrate was transferred into a 210 L reaction vessel having been heated at 60° C. and the container was washed with 2.01 L of dimethyl sulfoxide. To the solution, 18.9 kg of 2-propanol was added dropwise over 40 minutes, 15.02 g of crystals of the target compound was seeded, and 9.44 kg of 2-propanol was added dropwise over 57 minutes. After stirring the suspension at 60° C. for 1 hour and 30 minutes, the jacket temperature was set at 80° C. and the stirring was continued for 37 hours and 24 minutes. Then, 56.6 kg of 2-propanol was added dropwise to the suspension over 2 hours and 8 minutes, the mixture was cooled to 20° C. at a cooling rate of 10° C./hour and stirred at the same temperature for 65 hours and 50 minutes. The precipitated crystals were filtered, rinsed with a mixed solution of 534 mL of dimethyl sulfoxide and 4.81 L of 2-propanol and 8.01 L of 2-propanol in this order. The crystals were dried under reduced pressure at 50° C. to give 2.30 kg of the target product as yellow crystals (yield 90.8%).

PHARMACOLOGICAL TEST EXAMPLE

In order to confirm the effect of the compound of Example 10 as an antipruritic agent (PDE4 inhibitory action), the present inventors have conducted the following test.

Test Example 1

Evaluation of Compounds in Oxazolone-Induced Scratching Behavior Model

<Test Method>
As test animals, commercially available 5-week-old NC/Nga female mice (Japan SLC, Inc.) were used. For acclimation, the mice passed a preliminary breeding period of 7 days. Thereafter, only animals, wherein no changes were found in a general state and the body weight was favorably increased, were used for the test.

(1) Sensitization and Induction

Sensitization was carried out by applying once 204 of an acetone solution (Wako Pure Chemical Industries, Ltd.) that contained 0.5% 4-ethoxymethylene-2-phenyl-2-oxazolin-5-one (hereinafter abbreviated as "oxazolone"; Sigma) to each of the left and right pinnas of 6-week-old mice, which had passed an acclimation period.

Induction was carried out by applying 10 µl of 0.3% oxazolone to the left pinna of each mouse, 3 times in total, at the 5th day after sensitization, at 2 or 3 days after the 5th day after sensitization and at 2 or 3 days after said date.

(2) Measurement of Scratching Behavior

For objective evaluation, the scratching behavior of each mouse was automatically measured using a Micro Act device (NeuroScience, Inc.). A magnet piece (diameter: 1 mm; length: 3 mm; NeuroScience) was inserted into the skin of the left hind-leg of each mouse anesthetized with diethyl ether (Wako Pure Chemical Industries, Ltd.) by the day before the measurement at the latest. Immediately after scratching behavior had been induced by application of oxazolone, the mouse was transferred into a chamber (diameter: 11 cm; height: 18 cm) with a coil. Thereafter, electric current induced by the movement of the magnet inserted into the leg of the mouse was measured for a certain period of time. A characteristic wave form that reflects such scratching behavior was detected by the Micro Act device, and the appearance frequency of the detected wave form was counted as a number of scratching behaviors.

(3) Evaluation of Test Substance

Preparation of test substance: The compound of Example 10 was prepared at a concentration of 0.3% in a mixed solvent (acetone:ethanol=1:1).

With regard to the groups of test substances, the following 3 groups were determined: (1) normal group—a mixed solvent (acetone:ethanol=1:1) application group; (2) control group—a mixed solvent (acetone:ethanol=1:1) application group; (3) a compound of Example 10 application group. The mice were divided into each group, such that the number of scratching behaviors became uniform based on the number of scratching behaviors obtained during the 2nd induction.

Evaluation of test substance: Ten microliters of a test substance (only the mixed solvent (acetone:ethanol=1:1) was applied to the normal group and the control group) was administered 1 hour before the 3rd application of oxazolone. Evaluation of the test substance was carried out, using, as an indicator, the number of scratching behaviors obtained during 2 hours after induction due to the 3rd application of oxazolone (the mixed solvent (acetone:ethanol=1:1) was applied to the normal group). In addition, another evaluation was carried out based on cutaneous symptom. That is to say, with regard to findings of scratching behaviors obtained at 1 day before the 3rd application of oxazolone and at 1 day or 4 days after the application, namely, with regard to each of the items of (1) abrasion and (2) bleeding/erosion, 4 stages of rating ranging from 0 to 3 (0: no symptoms; 1: slight; 2: moderate; and 3: serious) was carried out. Thus, using the difference in scores obtained before and after induction with oxazolone as an indicator, the scratching behavior was evaluated. Such rating was carried out for every item, and the total score was defined as the score of each individual.

<Test Results>

Figure 1:
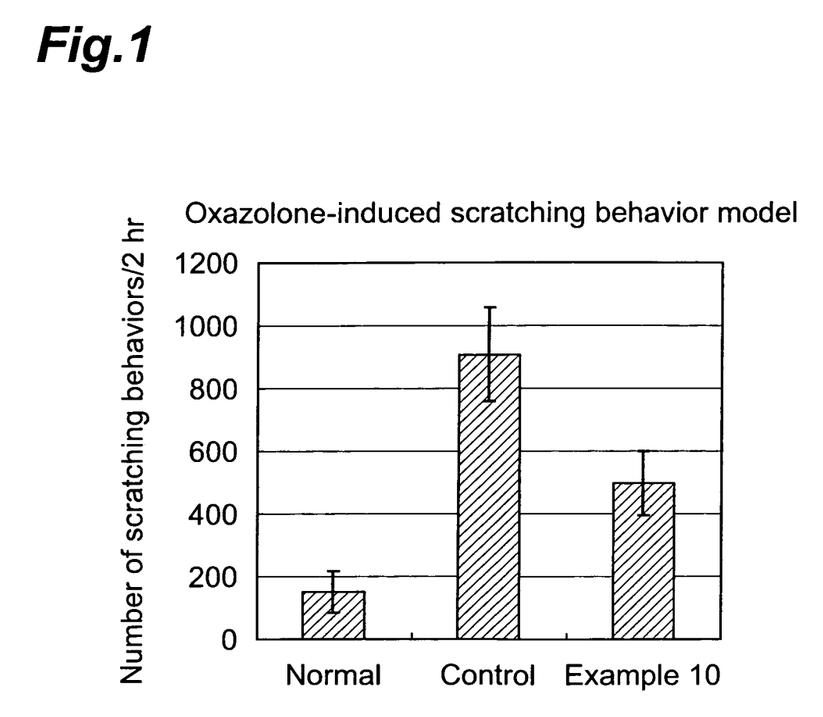
FIG. 1 shows the number of scratching behaviors of oxazolone-induced mice.

(1) The measurement results regarding the number of scratching behaviors are shown in FIG. 1 (normal group: n=11; the other groups: n=17 in FIG. 1).

Figure 2:
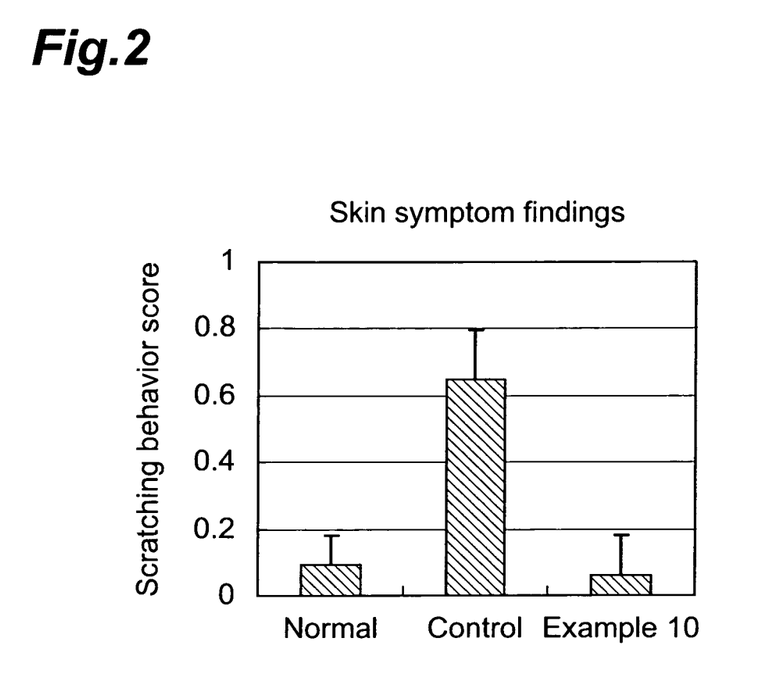
FIG. 2 shows the results of skin symptom findings (after 1 day) of oxazolone-induced mice.

(2) The measurement results regarding cutaneous symptoms are shown in FIG. 2. FIG. 2 is a graph made based on the value obtained by subtracting the score obtained before administration from the score obtained 1 day after administration (normal group: n=11; the other groups: n=17 in FIG. 2).

From these results, it was found that the compound of Example 10 suppress scratching behavior and also suppresses deterioration in cutaneous symptoms caused by such scratching behavior, thereby having an excellent antipruritic effect.

Test Example 2

Experiment to Evaluate Induction Potency of Drug Metabolizing Enzyme (CYP) Using Cryopreserved Human Hepatocytes <Test Operations>

Cryopreserved human hepatocytes (XenoTeck) were rapidly thawed at 37° C., and viable cells were obtained using Hepatocytes Isolation Kit (Nosan Corporation). After cells prepared were diluted with ice cold William's Medium E (10% FBS, +PSG) to give a concentration of $5 \times 10^5$ viable cells/mL, the cells were seeded onto a 48-well collagen-coated plate (BD Biosciences) at a concentration of $1 \times 10^5$ cells/cm$^2$ and cultured at 37° C. in 5% $CO_2$ for 24 hours. Then, the medium was replaced with Hepato-STIM (registered trade mark: BD Biosciences) (+EGF, PSG, −FBS), and the cells were further cultured at 37° C. in 5% $CO_2$ for 24 hours. Hepato-STIM(+EGF, PSG, −FBS) was used as culture medium, and the cells were incubated with culture medium containing test compound, β-naphthoflavone (hereinafter abbreviated as β-NF, SIGMA) used as a positive control of human CYP1A, or rifampicin (hereinafter abbreviated as Rif, Wako Pure Chemical Industries, Ltd.) used as a positive control of human CYP3A4 at 37° C. in 5% $CO_2$ for approximately 48 hours. The culture medium containing test compound, β-NF or Rif was replaced every 24 hours. Test compound, β-NF and Rif were each dissolved in dimethyl sulfoxide (DMSO: Wako Pure Chemical Industries, Ltd.), and culture medium containing test compound (final concentrations; 1, 3 and 10 µM), β-NF (final concentration; 10 µM) or Rif (final concentration; 10 µM) was prepared by adding them to Hepato-STIM(+EGF, PSG, −FBS), respectively. Final concentration of DMSO was set to be 0.1%, and culture medium containing 0.1% DMSO was used for control. After completion of the treatment, the cells were washed with PBS once, and total RNA was purified using Total RNA Purification Kit (Applied Biosystems). The purified total RNA was subjected to reverse transcription reaction using TaqMan Reverse Transcription Reagents (Applied Biosystems) to synthesize cDNA, where oligo dT was used as a primer. The reaction was carried out using GeneAmp PCR system 9700 at 25° C. for 10 minutes, followed by at 48° C. for 60 minutes. Then, reverse transcriptase was deactivated at 95° C. for 10 minutes. The levels of mRNA for CYP1A1 and GAPDH were quantified using SYBR Green PCR Core Reagents Kit (Applied Biosystems), and those for CYP1A2 and that of CYP3A4 were measured using Taqman PCR Core Reagents Kit (Applied Biosystems) and ABI Prism 7900 Sequence Detection System (Applied Biosystems). Primer sequences and PCR conditions used for quantification of each mRNA are shown in Tables 1 and 2, respectively.

Primer Sequences

TABLE 1

| Target | Name | Sequence |
|---|---|---|
| CYP1A1 | hCYP1A1_F1 | tggtctcccttctctacactcttgt (SEQ ID NO: 1) |
| | hCYP1A1_R1 | attttccctattacattaaatcaatggttct (SEQ ID NO: 2) |
| CYP1A2 | hCYP1A2_F_EJCP | gttcctgcagaaaacagtcca (SEQ ID NO: 3) |
| | hCYP1A2_R_EJCP | ctgtgcttgaacagggcac (SEQ ID NO: 4) |
| | hCYP1A2_probe_EJCP | agcactatcaggactttgacaagaacagtgtct (SEQ ID NO: 5) |
| CYP3A4 | hCYP3A4_F_m | gcaggaggaaattgatgcagtt (SEQ ID NO: 6) |
| | hCYP3A4_R_x | gtcaagatactccatctgtagcacagt (SEQ ID NO: 7) |
| | hCYP3A4_probe_m | Acccaataaggcaccacccacctatga (SEQ ID NO: 8) |
| GAPDH | hGAPDH_F | gaaggtgaaggtcggagtc (SEQ ID NO: 9) |
| | hGAPDH_R | gaagatggtgatgggatttc (SEQ ID NO: 10) |

PCR Conditions

TABLE 2

| Temperature | Time | |
|---|---|---|
| 95 | 10 min | |
| 94 | 15 sec | Denaturation |
| 58 | 20 sec | Annealing |
| 72 | 30 sec | Elongation reaction |

* A cycle consisting of denaturation, annealing, and elongation reaction, was repeated 50 times.

<Calculation of Ability to Induce CYP>
The ability of a test compound to induce CYP1A1 was calculated as follows:

Ability of a test compound to induce CYP1A1(%)=
{[(amount of mRNA of CYP1A1 in test compound treated cells)/(amount of mRNA of GAPDH in test compound treated cells)]/[(amount of mRNA of CYP1A1 in control cells)/(amount of mRNA of GAPDH in control cells)]−1}/{[(amount of mRNA of CYP1A1 in positive control treated cells)/(amount of mRNA of GAPDH in positive control treated cells)]/[(amount of mRNA of CYP1A1 in control cells)/(amount of mRNA of GAPDH in control cells)]−1}×100

The ability to induce CYP1A2 or CYP3A4 was calculated in the same manner described above.

<Test Results>
The results regarding the compound of Example 10 are shown in Table 3. As a comparative example, the compound described as Example 1 in WO99/37622 (4-(3-benzoylaminophenyl)-6,7-dimethoxy-2-methylaminoquinalozine) was used.

The results indicated that the compound of Example 10 shows lower induction potency on CYPs than the compound of the comparative example.

TABLE 3

| | | Induction Ability compared to positive control (%) | | |
|---|---|---|---|---|
| | | CYP1A1 | CYP1A2 | CYP3A4 |
| Rifampicin | 10 μM | | | 100.0 |
| β-naphthoflavone | 10 μM | 100.0 | 100.0 | |
| Example 1 | 1 μM | 0.1 | −0.1 | −2.4 |
| | 3 μM | 0.6 | −0.7 | −3.4 |
| | 10 μM | 4.6 | 2.5 | −4.0 |
| Comparative example | 1 μM | 2.1 | 7.2 | 1.6 |
| | 3 μM | 18.5 | 34.3 | 10.8 |
| | 10 μM | 51.9 | 35.0 | 17.0 |

INDUSTRIAL APPLICABILITY

The present invention can provide a method for producing a compound that serves as a drug useful for itch of atopic disease or the like and a production intermediate that can be used in this production method.

The invention claimed is:

1. A method for producing [4-(3-aminophenyl)-6,7-dimethoxyquinazolin-2-yl]methylamine, comprising subjecting a compound represented by the following formula (I):

(I)

wherein L represents a protective group of amino to a step of reacting with methylamine.

2. The production method according to claim 1, wherein the compound represented by the formula (I):

(I)

wherein L represents a protective group of amino is obtained by reacting 2,4-dichloro-6,7-dimethoxyquinazoline with a compound represented by the following formula (II):

(II)

wherein L represents a protective group of amino, and X represents —B(OH)$_2$, —B(OR$^1$)(OR$^2$) where R$^1$ and R$^2$ each independently represent hydrogen or C$_{1-6}$ alkyl or R$^1$ and R$^2$ represent together dimethylmethylene, 1,2-ethylene, 1,3-propylene, or 2,3-dimethyl-butane-2,3-diyl, or —BF$_3$M where M represents sodium or potassium.

3. The production method according to claim 1, wherein L represents formyl, t-butoxycarbonyl, or acetyl.

4. A compound, which is:
t-Butyl[3-(2-chloro-6,7-dimethoxyquinazolin-4-yl)phenyl]carbamate,
N-[3-(2-chloro-6,7-dimethoxyquinazolin-4-yl)phenyl]formamide, or
N-[3-(2-chloro-6,7-dimethoxyquinazolin-4-yl)phenyl]acetamide.

5. The production method according to claim 2, wherein L represents formyl, t-butoxycarbonyl, or acetyl.

6. The production method according to claim 1, further comprising a step of deprotection.

7. The production method according to claim 6, wherein the compound represented by the formula (I):

wherein L represents a protective group of amino is obtained by reacting 2,4-dichloro-6,7-dimethoxyquinazoline with a compound represented by the following formula (II):

wherein L represents a protective group of amino, and X represents —B(OH)$_2$, —B(OR$^1$)(OR$^2$) where R$^1$ and R$^2$ each independently represent hydrogen or C$_{1-6}$ alkyl or R$^1$ and R$^2$ represent together dimethylmethylene, 1,2-ethylene, 1,3-propylene, or 2,3-dimethyl-butane-2,3-diyl, or —BF$_3$M where M represents sodium or potassium.

8. The production method according to claim 6, wherein L represents formyl, t-butoxycarbonyl, or acetyl.

* * * * *